(12) United States Patent
Nakagawa

(10) Patent No.: US 7,159,447 B2
(45) Date of Patent: Jan. 9, 2007

(54) GAS SENSOR EQUIPPED WITH GAS INLET DESIGNED TO CREATE DESIRED FLOW OF GAS

(75) Inventor: Kazuya Nakagawa, Kariya (JP)

(73) Assignee: Denso Corporation (JP)

( * ) Notice: Subject to any disclaimer, the term of this patent is extended or adjusted under 35 U.S.C. 154(b) by 77 days.

(21) Appl. No.: 11/055,012

(22) Filed: Feb. 11, 2005

(65) Prior Publication Data
US 2005/0178187 A1 Aug. 18, 2005

(30) Foreign Application Priority Data
Feb. 13, 2004 (JP) .............................. 2004-037222

(51) Int. Cl.
*G01N 27/00* (2006.01)
*G01N 37/00* (2006.01)
(52) U.S. Cl. ................. 73/31.05; 73/23.2; 73/23.31; 204/424; 204/428; 204/430
(58) Field of Classification Search ................. 73/23.2, 73/23.31, 31.05; 204/421, 424, 425, 426, 204/427, 428, 429, 430, 431
See application file for complete search history.

(56) References Cited

U.S. PATENT DOCUMENTS

| 4,507,192 A | 3/1985 | Ebizawa et al. |
| 6,279,376 B1 | 8/2001 | Yamada et al. |
| 6,346,179 B1 | 2/2002 | Makino et al. ............. 204/428 |
| 2003/0121782 A1 | 7/2003 | Atsumi et al. |

FOREIGN PATENT DOCUMENTS

| DE | 19924319 A1 | 12/2000 |
| EP | 1236998 A2 | 9/2002 |
| JP | 2001-99807 | 4/2001 |
| WO | WO 00/73779 A1 | 5/1999 |

OTHER PUBLICATIONS

French Preliminary Search Report dated Apr. 12, 2006.

*Primary Examiner*—Daniel S. Larkin
(74) *Attorney, Agent, or Firm*—Nixon & Vanderhye PC

(57) ABSTRACT

A gas sensor equipped with a protective gas cover which defines therein a gas chamber to which a sensor element is exposed. The protective gas cover has gas inlet holes through which gas to be measured is admitted. The protective cover also has dimples formed adjacent the gas inlet holes, respectively, which are designed to avoid a direct hit of a flow of the gas on the sensor element and minimize the concentration of thermal stress around the gas inlet holes. In an alternative form, the gas inlet holes are formed in the dimples, respectively.

9 Claims, 10 Drawing Sheets

US 7,159,447 B2

GAS SENSOR EQUIPPED WITH GAS INLET DESIGNED TO CREATE DESIRED FLOW OF GAS

CROSS REFERENCE TO RELATED DOCUMENT

The present application claims the benefit of Japanese Patent Application No. 2004-37222 filed on Feb. 13, 2004, the disclosure of which is incorporated herein by reference.

BACKGROUND OF THE INVENTION

1. Technical Field of the Invention

The present invention relates generally to a gas sensor which may be installed in an exhaust system of an internal combustion engine to determine the concentration of $O_2$, an air-fuel ratio, or the concentration of NOx in exhaust emissions, and more particularly to an improved structure of such a type of gas sensor equipped with gas inlets designed to create a desired flow of gas to be measured and minimize the concentration of thermal stress around the gas inlets.

2. Background Art

Conventionally, gas sensors are used for burning control of internal combustion engines for automotive vehicles. As a typical example, a gas sensor is installed in an exhaust pipe of an automotive engine to measure the concentration of a specified gas contained in exhaust emission of the engine. A gas sensor of this type consists essentially of a gas sensor element disposed within a hollow cylindrical housing, an air cover installed on a base portion of the housing, and a protective gas cover installed on a tip portion of the housing. The gas cover has formed therein a plurality of gas inlet holes through which a gas to be measured is admitted.

For example, U.S. Pat. No. 6,346,179 B1 (Japanese Patent First Publication No. 2001-99807) discloses a unique structure of a protective gas cover as used in a gas sensor.

FIGS. 9 and 10 show an example of a protective gas cover of the type as described above.

The protective gas cover 91 is usually required to be designed to minimize a direct hit of a flow of gas to be measured on the sensor element exposed inside the protective gas cover.

In the case where it is only required to draw a flow of gas into the protective gas cover 91, the protective gas cover 91 may have gas inlet holes 910 formed by merely punching out a side wall thereof. Although not illustrated, additional gas inlets may be formed in a straight section of the side wall beneath the gas inlet holes 910.

Usually, exhaust gases emitted from automotive engines contain various harmful substances which result in accelerated deterioration of the sensor element 2. The structure of the gas inlet holes 910 results in a flow of the gas which is, as indicated by an arrow m in FIG. 9, oriented to cause a direct hit on an outer surface of the sensor element 2, so that the sensor element 2 is exposed to the harmful substances, thus leading to the accelerated deterioration of the sensor element 2.

To encourage an approach to solution of the above drawback, there has been proposed a protective gas cover, as demonstrated in FIGS. 11 and 12.

The protective cover 92 has gas inlet holes 920 each equipped with a louver which is designed to avoid a direct hit of the gas on the sensor element 2. Each of the louvers is formed by making a U-shaped cut 922 in the side wall of the gas cover 92 to form a tab 970 and bending the tab 970 inwardly of the gas cover 92 at a base 923 of the tab 970. The louvers, as illustrated in FIG. 11, serve to create flows of the gas oriented upward, as indicated by arrows n, thereby avoiding a direct hit of the gas on the sensor element 2.

The louvers of the illustrated type are, however, lower in mechanical strength at the base 923. When exposed to hot exhaust gas of the engine, the base 923 undergoes a great degree of thermal stress, which may, as illustrated in FIG. 12, result in cracks 921 extending from the cut 922.

SUMMARY OF THE INVENTION

It is therefore an object of the invention to provide an improved structure of a gas sensor equipped with gas inlets designed to avoid a direct hit of a flow of gas to be measured on a sensor element and minimize the concentration of thermal stress around the gas inlets.

According to one aspect of the invention, there is provided a gas sensor which may be employed in measuring the concentration of a specified gas contained in exhaust emissions of an internal combustion engine of an automotive vehicle. The gas sensor comprises: (a) a hollow cylindrical housing having a first end and a second end opposite to the first end; (b) a gas sensing element having a sensing portion, the gas sensing element being retained within the housing through a porcelain insulator to expose the sensing portion outside the first end of the housing; and (c) a cover secured at an end thereof to the first end of the housing to define a gas chamber to which the sensing portion of the gas sensing element is exposed. The cover has a dimple and a gas inlet hole. The dimple leads to a periphery of the gas inlet hole.

The dimple is designed to create a desired flow of gas to be measured into the cover which is oriented to avoid a direct hit of the flow of the gas on the gas sensing element and to minimize the concentration of thermal stress around the gas inlet hole.

In the preferred mode of the invention, the gas sensor further comprises an outer cover which has a first end and a second end opposite to the first end and is secured at the first end thereof to the first end of the housing and disposed outside the cover. The outer cover has a gas inlet hole through which a gas to be measured is admitted to the gas chamber.

The gas inlet hole of the outer cover is located closer than the gas inlet hole of the cover to the second end of the outer cover. This creates a flow of the gas oriented from the second end to the first end of the outer cover, thereby minimizing the possibility of a direct hit of the gas on the gas sensing element.

The cover may have a tapered wall continuing to the end thereof joined to the first end of the housing, the tapered wall having a diameter which increases as the wall approaches the end of the cover. The gas inlet hole may be formed in the tapered wall of the cover.

The gas inlet hole of the cover may have a peripheral edge oriented to a second end of the cover remote from the end joined to the first end of the housing. The dimple has a wall leading to the peripheral edge of the gas inlet hole of the cover.

The dimple has a curved surface oriented to the gas inlet hole of the cover.

According to the second aspect of the invention, there is provided a gas sensor which comprises: (a) a hollow cylindrical housing having a first end and a second end opposite to the first end; (b) a gas sensing element having a sensing portion, the gas sensing element being retained within the housing through a porcelain insulator to expose the sensing portion outside the first end of the housing; and (c) a cover secured at an end thereof to the first end of the housing to define a gas chamber to which the sensing portion of the gas sensing element is exposed. The cover has a dimple and a gas inlet hole which is formed in the dimple.

In the preferred mode of the invention, the gas sensor may further include an outer cover which is disposed outside the cover. The outer cover has a gas inlet hole through which a gas to be measured is admitted to the gas chamber.

The gas inlet hole of the outer cover is located farther than the gas inlet hole of the cover from the first end of the housing.

The dimple has a curved wall in which the gas inlet hole is formed. The dimple may be of a domed shape.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

Figure 1:
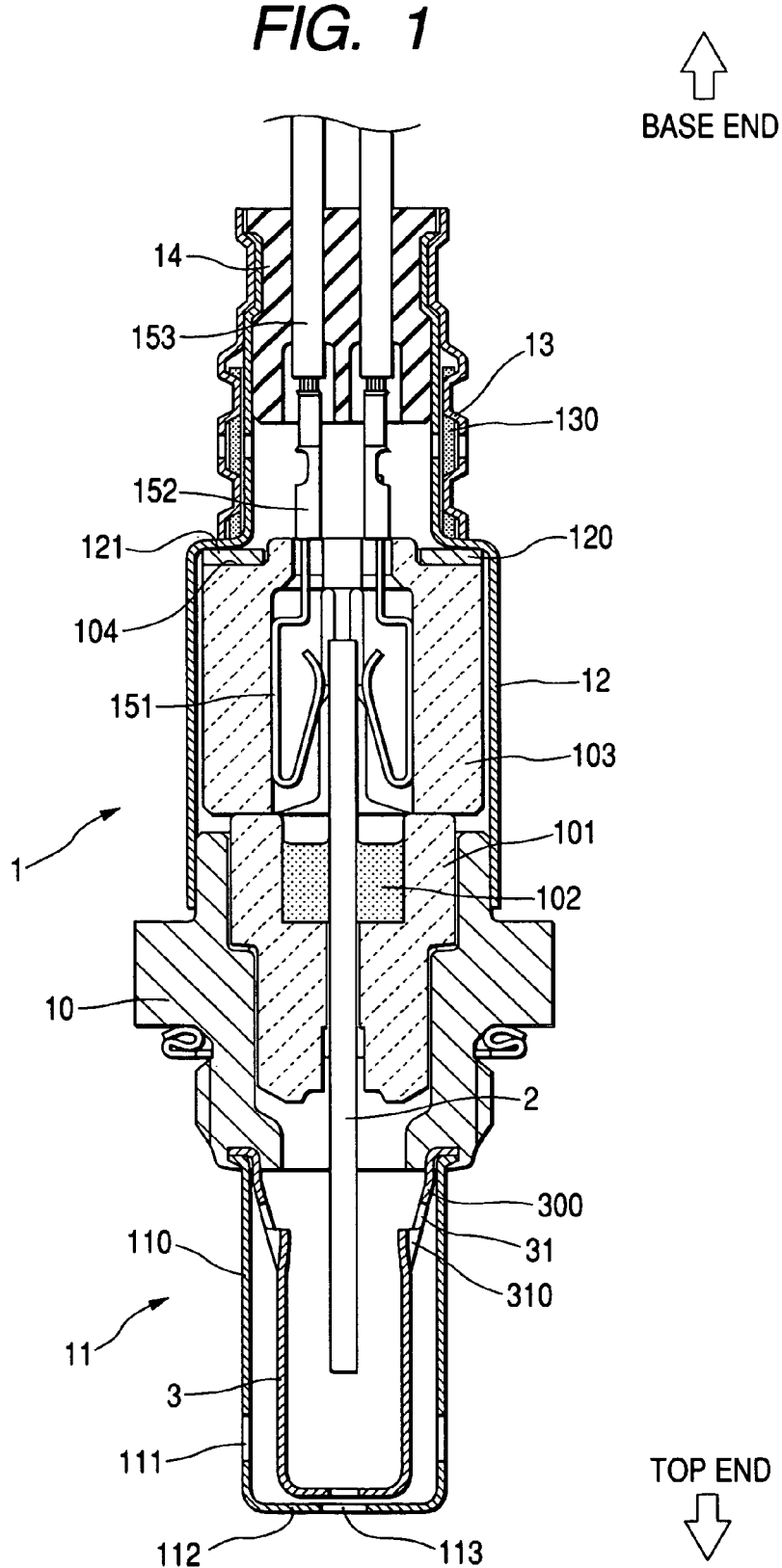
FIG. 1 is a longitudinal sectional view which shows a gas sensor equipped with a protective cover assembly according to the first embodiment of the invention.
Figure 4A:
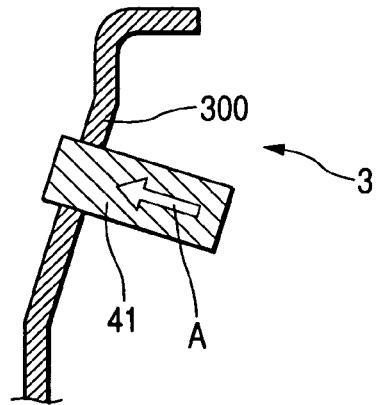
Figure 4B:
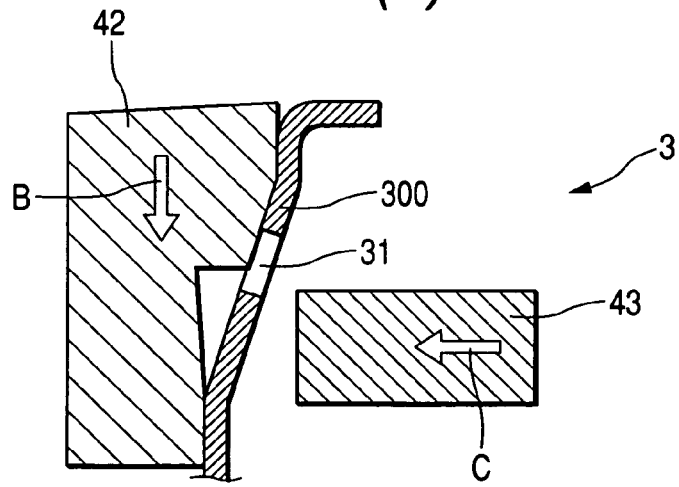
Figure 4C:
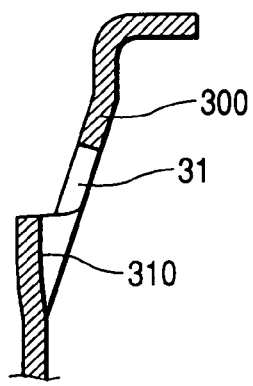
Figure 5:
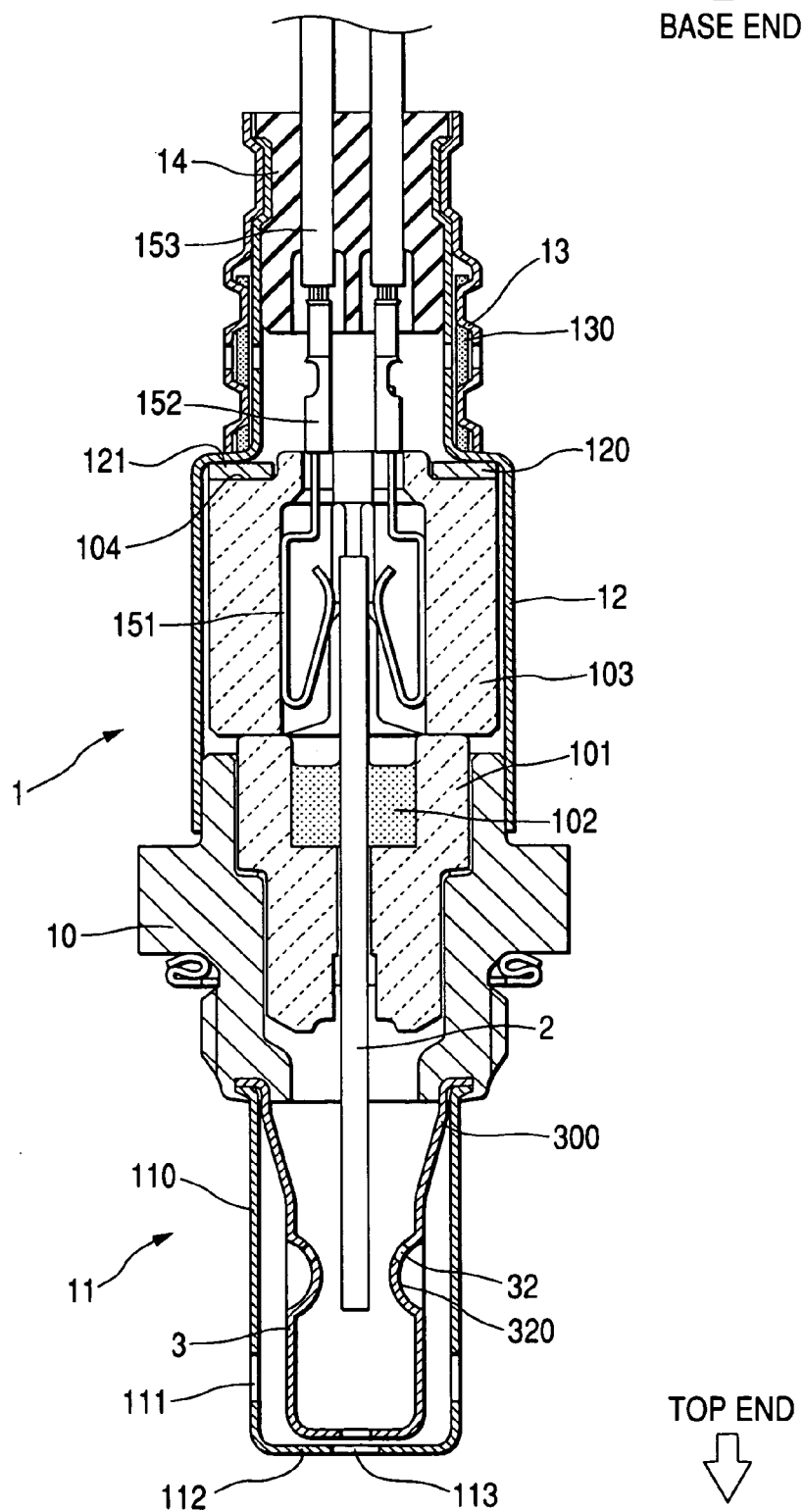
Figure 6:
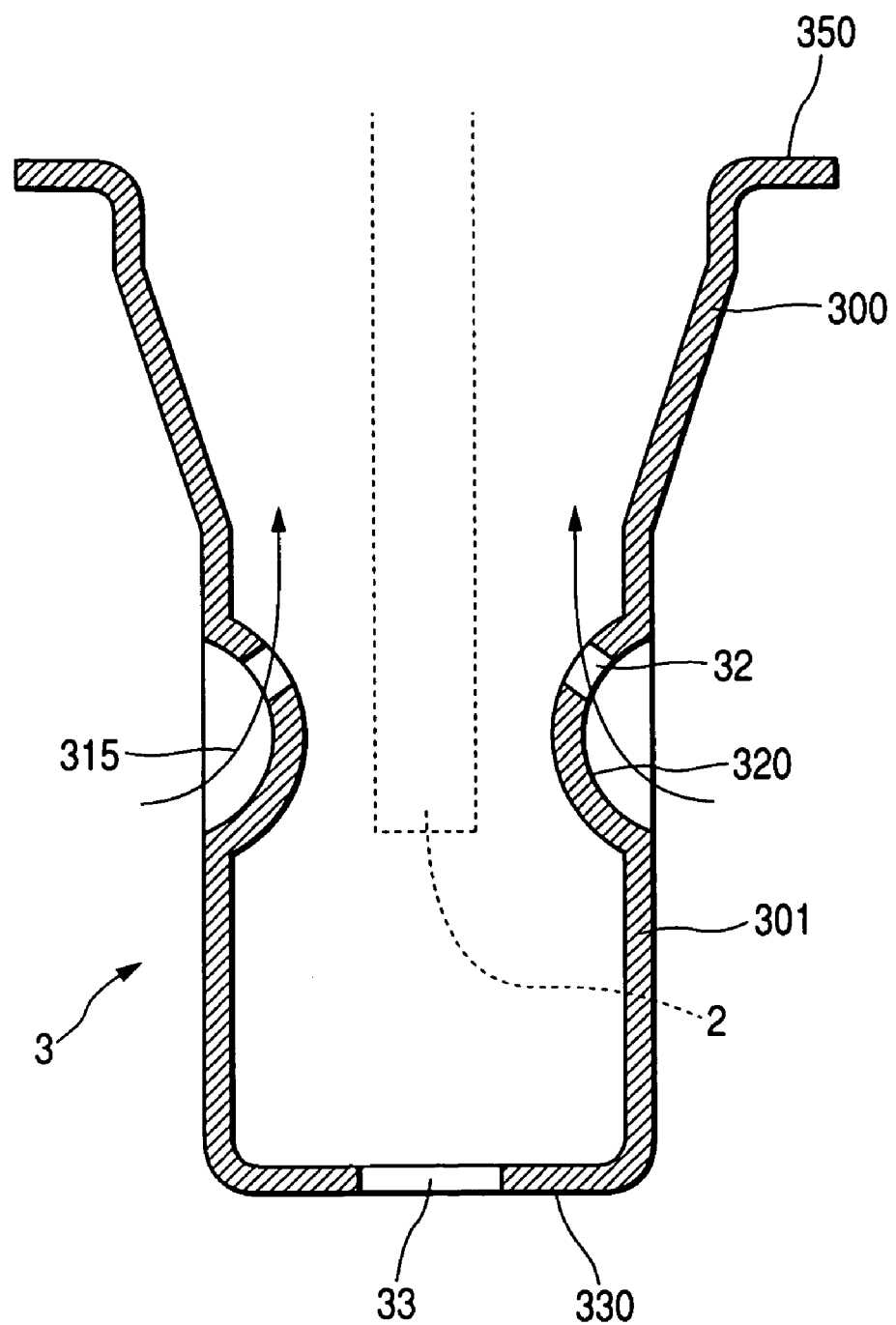
Figure 7:
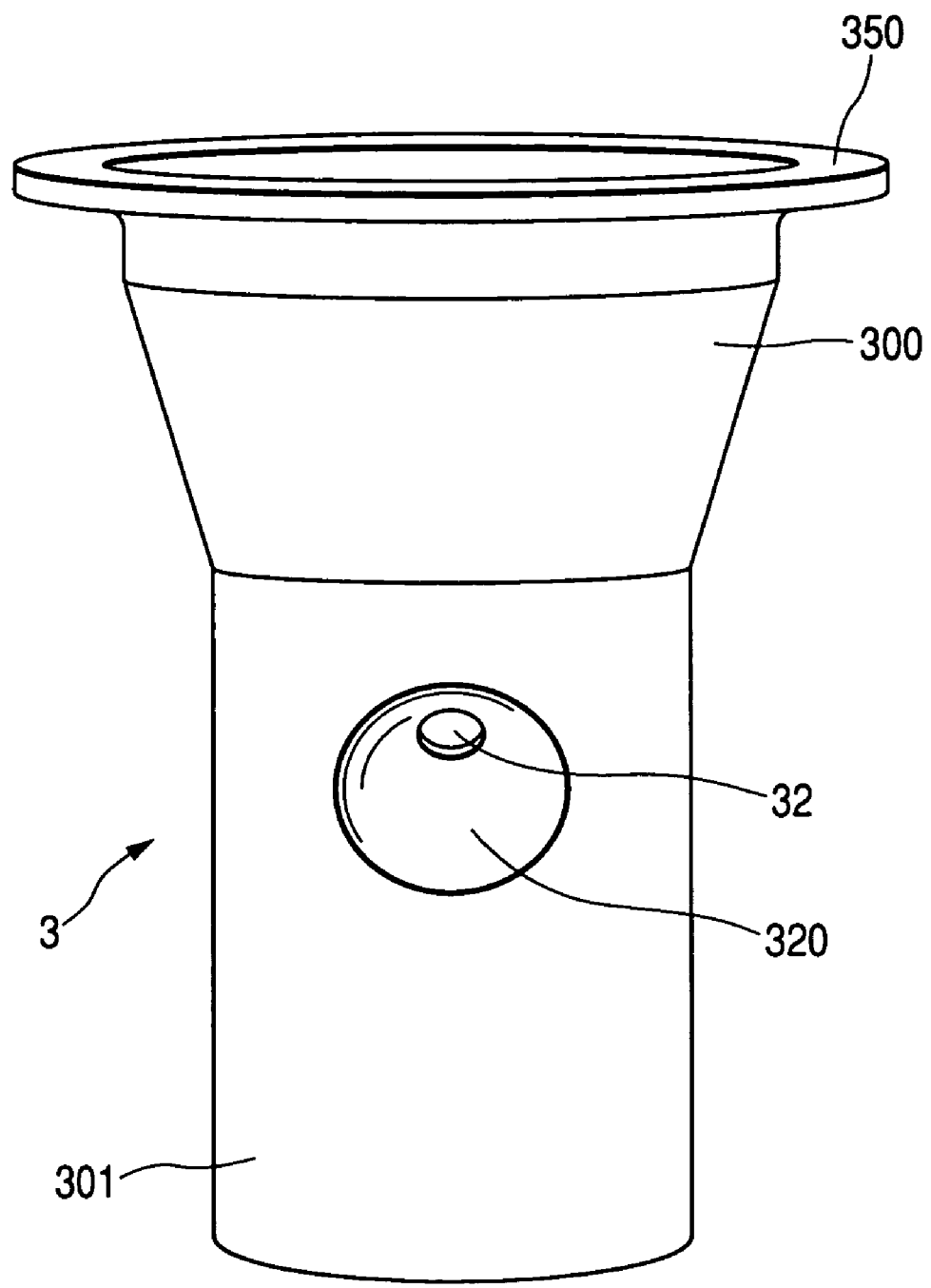
Figure 8A:
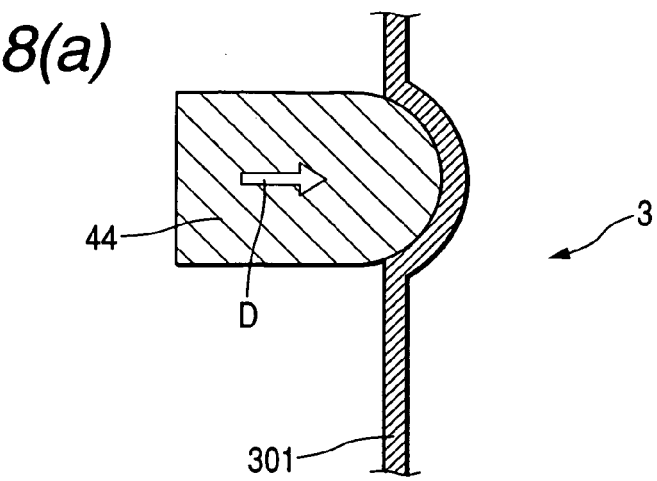
Figure 8B:
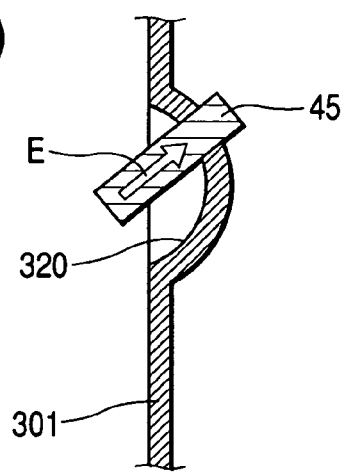
Figure 8C:
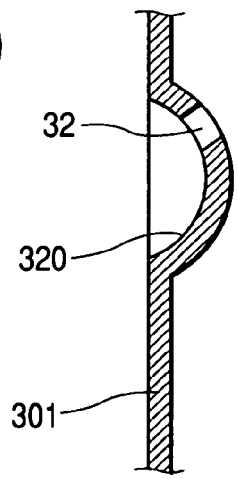
Figure 9:
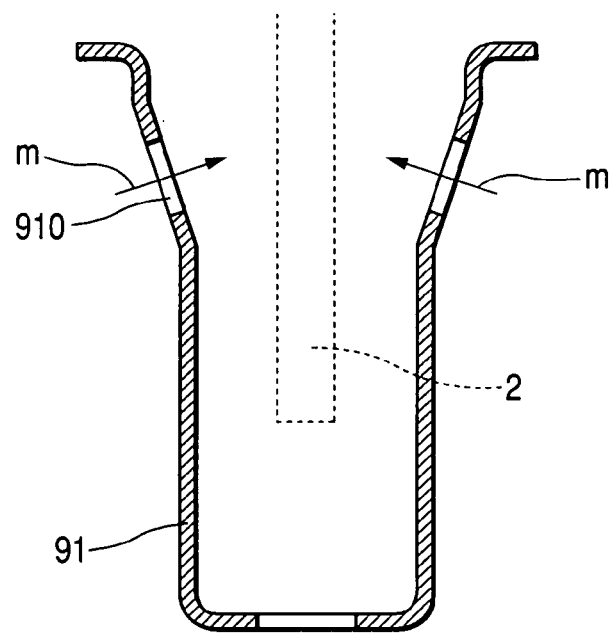
Figure 10:
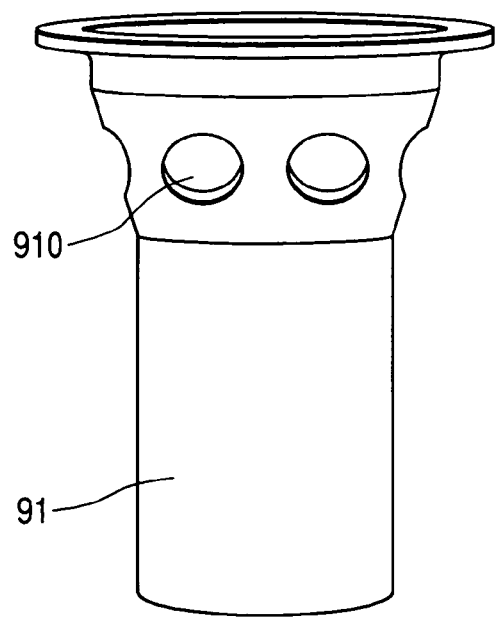
Figure 11:
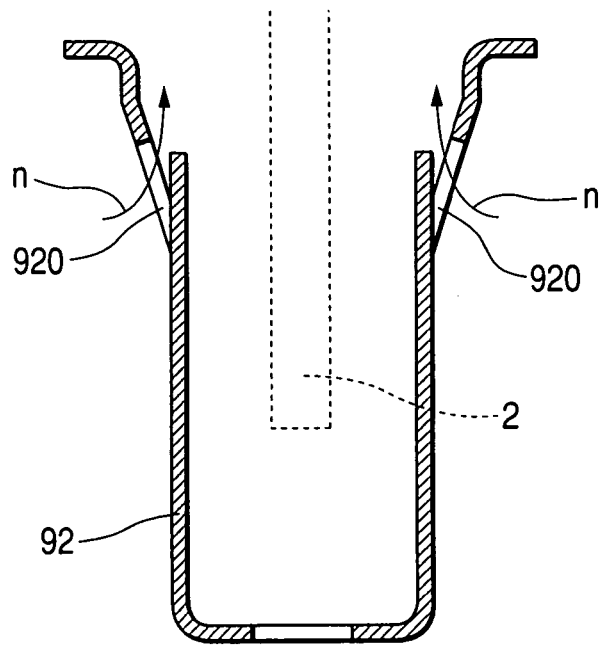
Figure 12:
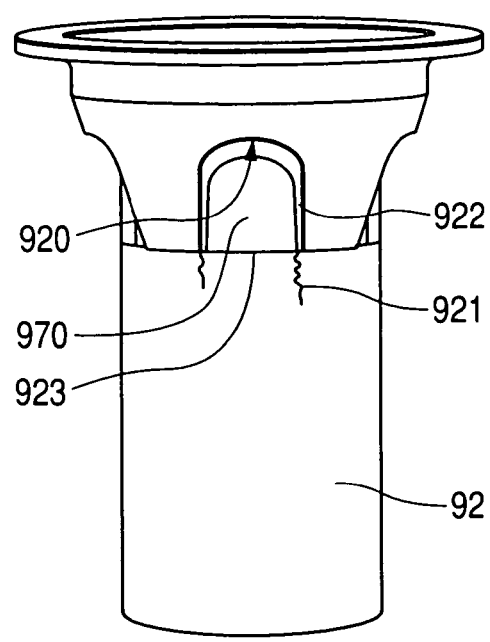

FIGS. 4(a), 4(b), and 4(c) are partially sectional views which shows a sequence of steps of forming a gas inlet hole and a dimple in an inner cover of the protective cover assembly, as illustrated in FIG. 1;

FIG. 5 is a longitudinal sectional view which shows a gas sensor equipped with a protective cover assembly according to the second embodiment of the invention;

FIG. 6 is a longitudinal sectional view which shows an inner cover of the protective cover assembly, as illustrated in FIG. 5;

FIG. 7 is a perspective view which shows an inner cover of the protective cover assembly, as illustrated in FIG. 5;

FIGS. 8(a), 8(b), and 8(c) are partially sectional views which shows a sequence of steps of forming a gas inlet hole and a dimple in an inner cover of the protective cover assembly, as illustrated in FIG. 5;

FIG. 9 is a longitudinal sectional view which shows an example of a conventional gas cover;

FIG. 10 is a perspective view which shows the gas cover of FIG. 9;

FIG. 11 is a longitudinal sectional view which shows a second example of a conventional gas cover; and FIG. 12 is a perspective view which shows the gas cover of FIG. 11.

DESCRIPTION OF THE PREFERRED EMBODIMENTS

Referring to the drawings, wherein like reference numbers refer to like parts in several views, particularly to FIG. 1, there is shown a gas sensor 1 according to the first embodiment of the invention which may be employed in a burning control system for automotive engines to measure the concentration of a gas component, such as $O_2$ or NOx, contained in exhaust gasses of the engine.

The gas sensor 1 generally includes a gas sensor element 2, a hollow cylindrical housing 10, a porcelain insulator 101, and a protective cover assembly 11. The gas sensor element 2 is retained in the housing 10 through the porcelain insulator 101. The protective cover assembly 11 is secured to a top end (i.e., a lower end as viewed in the drawing) of the housing 10.

The protective cover assembly 11 has a length extending in alignment with the longitudinal center line of the gas sensor 1 (i.e., the gas sensor element 2). The protective cover assembly 11 has a double-walled structure consisting of a cylindrical outer cover 110 and a cylindrical inner cover 3 disposed inside the outer cover 110. The outer cover 110 has a plurality of gas inlet holes 111 formed in a side wall thereof. The inner cover 3, as clearly shown in FIGS. 2 and 3, has formed in a side wall thereof a plurality of gas inlet holes 31 and recesses or dimples 310 each leading to a peripheral edge of one of the gas inlet holes 31. The inner and outer covers 3 and 110 have flanges installed on the top end of the housing 10 to define a gas chamber within which a sensing portion of the gas sensor element 2 is disposed and into which a gas to be measured (will also be referred to as a measurement gas below) is admitted through gas inlet holes 31 and 111.

Figure 2:
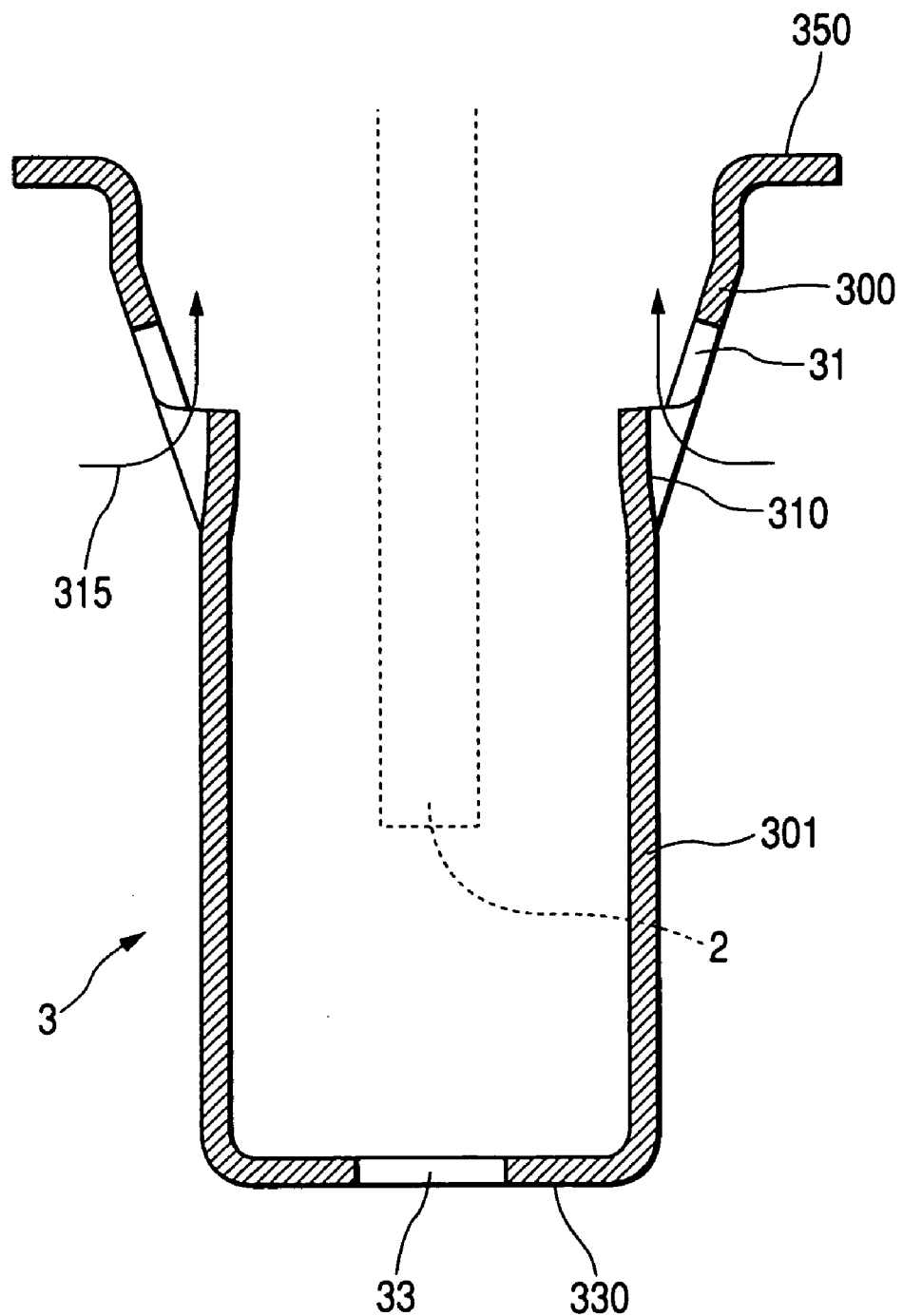
FIG. 2 is a longitudinal sectional view which shows an inner cover of the protective cover assembly, as illustrated in FIG. 1.
Figure 3:
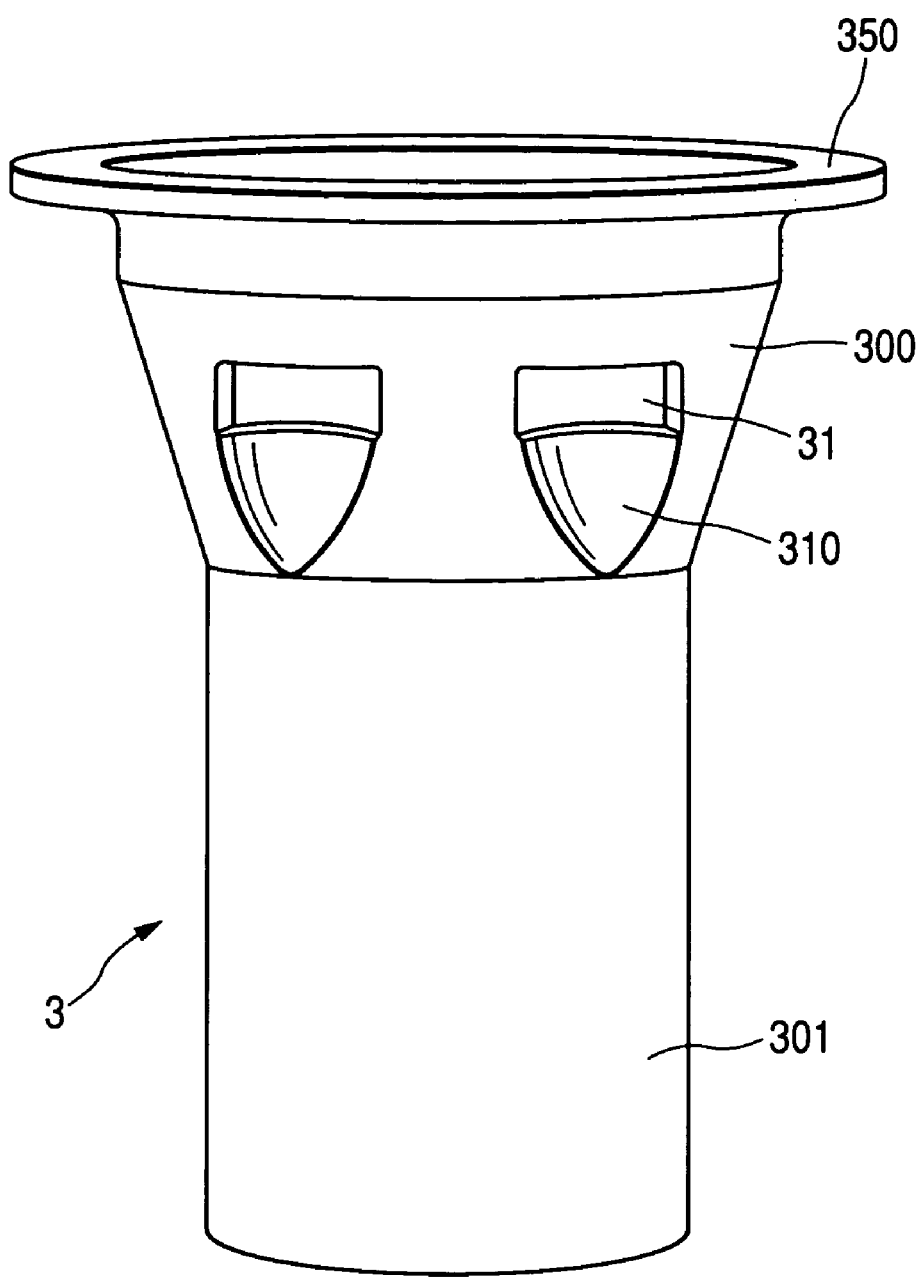
FIG. 3 is a perspective view which shows an inner cover of the protective cover assembly, as illustrated in FIG. 1.

The side wall of the outer cover 110, as can be seen in FIG. 1, extends straight in the lengthwise direction of the protective cover assembly 11. The inner cover 3 includes, as illustrated in FIGS. 2 and 3, a straight side wall 301 and a tapered side wall 300 formed closer to the flange 350. The tapered side wall 300 is of a cone-shape whose diameter increases as the wall approaches the flange 350 and has the gas inlet holes 31 formed therein. The gas inlet holes 31 are located closer to the top end of the housing 10 than the gas inlet holes 111 of the outer cover 110. In other words, the gas inlet holes 111 are located closer than the gas inlet holes 31 to the top end of the gas sensor 1 exposed to the measurement gas flowing outside the gas sensor 1. This results in a flow of the measurement gas within a space between the outer and inner covers 110 and 3 which is oriented toward the top end of the housing 10 (i.e., upward as viewed in FIG. 1), thereby directing harmful substances contained in the measurement gas toward the bottom 112 of the outer cover 110. This minimizes exposure of the sensor element 2 to the harmful substances. The gas inlet holes 31 are, as described above, formed in the tapered side wall 300 of the inner cover 3 and thus serve to permit the upwardly oriented flow of the measurement gas to enter the inner cover 3 without disturbance.

Each of the dimples 310 is of a substantially triangular shape and has one side coinciding with a lower edge of one of the gas inlet holes 31.

Referring back to FIG. 1, the gas sensor 1 also includes an air cover 12 and an outer cover 13. The outer cover 13 is provided around the air cover 12 and staked or crimped to retain a cylindrical water-repellent filter 130 on the periphery of the air cover 12.

The gas sensor element 2 is fitted within the cylindrical porcelain insulator 101 through a glass seal 102. The glass seal 102 is disposed within the porcelain insulator 101 to establish an air-tight seal between the gas sensor element 2 and the porcelain insulator 101.

The gas sensor element 2, as described above, has the sensing portion exposed to the measurement gas having entered the protective cover assembly 11 and a base end portion disposed inside the air cover 12. The base end portion has formed thereon electrode pads (not shown) which are in electrical contact with spring terminals 151.

The spring terminals 151 connect with connectors (e.g., crimp contacts) 152 in which leads 153 are accepted. The leads 153 extend to connect with an external device (not shown) for transmission of sensor signals between the gas sensor element 2 and the external device and supply of electric power to a heater (not shown) installed in the gas sensor element 2.

An elastic insulator 14 is fitted within a base end portion of the air cover 12 firmly by crimping the outer cover 13 to retain the leads 153 inside the insulator 14 tightly.

The air cover 12 has a shoulder 121. An upper porcelain insulator 103 is disposed on the porcelain insulator 101 within the air cover 12. A disc spring 120 is disposed between an inner wall of the shoulder 121 and a base end surface 104 of the upper porcelain insulator 103.

The outer cover 110 is made of a hollow cylinder with the bottom 112 and has a diameter uniform over the length thereof. The gas inlet holes 111 are formed in a portion of the side wall of the outer cover 110 closer to the bottom 112 than the gas inlet holes 31 of the inner cover 3. The bottom 112 of the outer cover 110 has a circular hole 113 formed in the center thereof.

The inner cover 3 is, as clearly shown in FIGS. 2 and 3, made of a hollow cylinder with a bottom 330. The bottom 330 has a circular hole 33 formed in the center thereof to coincide with the hole 113 of the outer cover 110. The inner cover 3, as described above, has the tapered side wall 300 formed on a base end side thereof. The tapered side wall 300 has six gas inlet holes 31 arranged in a circumferential direction thereof at regular intervals. Each of the gas inlet holes 31 is substantially rectangular and has an edge closer to the bottom 330 which leads to one of the dimples 310. Each of the dimples 310 has a curved triangular wall whose one side coincides with the downstream edge of one of the gas inlet holes 31, thereby resulting in a flow of the measurement gas oriented substantially parallel to the length of the protective cover assembly 11. This minimizes the possibility of a direct hit of the flow of the measurement gas on the gas sensor element 2 to avoid exposure of the gas sensor element 2 to harmful substances contained in the measurement gas.

The manner of forming the gas inlet holes 31 and the dimples 310 in the inner cover 3 will be described below with reference to FIGS. 4(a) to 4(c).

First, a punch 41 is, as illustrated in FIG. 4(a), advanced in a direction, as indicated by an arrow A, and pressed against a preselected portion of the tapered side wall 300 to punch out each of the gas inlet holes 31.

Next, a die 42, as illustrated in FIG. 4(b), is inserted into the inner cover 3 in a direction, as indicated by an arrow B, and placed in abutment with the inner surface of the inner cover 3 near the gas inlet hole 31. Subsequently, a press punch 43 is forced against a portion of the outer surface of the inner cover 3 beneath the gas inlet hole 31 in a direction, as indicated by an arrow C, until the portion abuts the wall of the die 42, thereby forming the dimple 310, as illustrated in FIG. 4(c).

Each of the dimples 310 functions to create, as illustrated in FIG. 2, a flow 315 of the measurement gas oriented upward, as viewed in the drawing, and direct it into the gas inlet hole 31 without a hit on the gas sensor element 2.

The gas inlet holes 31 are not equipped with a louver such as the one, as illustrated in FIGS. 11 and 12, and thus insensitive to damage arising from the concentration of thermal stress therearound. Specifically, the structure of the inner cover 3 is effective to avoid the direct hit of the gas flow on the sensing portion of the gas sensor element 2 and minimize the concentration of thermal stress on the inner cover 3 around the gas inlet holes 31.

The protective cover assembly 11 may alternatively include only the inner cover 3 which is disposed so that it may be exposed directly to the measurement gas flowing outside the gas sensor 1.

FIG. 5 shows a gas sensor 1 according to the second embodiment of the invention. The same reference numbers will refer to the same parts in the first embodiment, and explanation thereof in detail will be omitted here.

The gas sensor 1 includes the protective cover assembly 11, like the first embodiment, which is made up of the cylindrical outer cover 110 and the cylindrical inner cover 3 disposed inside the outer cover 110. The outer cover 110 has the gas inlet holes 111 formed in a side wall thereof. The inner cover 3, as clearly shown in FIGS. 6 and 7, has formed in the side wall 301 thereof gas inlet holes 32 and dimples 320 which are recessed inwardly and arranged in a circumferential direction thereof. The dimples 320 are located beneath the tapered side wall 300. Each of the gas inlet holes 32 is formed in an upper portion (as viewed in FIG. 6) of a curved wall of one of the dimples 320 which is closer to the base end (i.e., the flange 350). In other words, the gas inlet holes 32 open into the gas chamber in the inner cover 3 in an obliquely upward direction.

The gas inlet holes 111 of the outer cover 110 are located closer to the top end of the gas sensor 1 (i.e., the bottom 112 of the outer cover 110) than the gas inlet holes 32 of the inner cover 3. This results in a flow of the measurement gas within a space between the outer and inner covers 110 and 3 which is oriented toward the top end of the housing 10 (i.e., upward as viewed in FIG. 5), thereby directing harmful substances contained in the measurement gas toward the bottom 112 of the outer cover 110. This minimize exposure of the gas sensor element 2 to the harmful substances. The gas inlet holes 32 are, as described above, formed in the upper portions of the dimples 320 and thus serve to permit the upwardly oriented flow of the measurement gas to enter the inner cover 3 without disturbance.

The side wall of the outer cover 110, as can be seen in FIG. 5, extends straight in the lengthwise direction of the protective cover assembly 11. The side wall 301 of the inner cover extends straight in the lengthwise direction of the protective cover assembly 11. The dimples 320 are, as can be seen from FIG. 6, positioned in locations on the inner cover 3 diametrically opposed to each other 180° apart. Each of the dimples 320 is of a substantially domed shape and recessed inwardly of the inner cover 3. Each of the gas inlet holes 32 is formed in a portion of one of the dimples 320 which is slightly closer to the base end (i.e., the flange 350) of the inner cover 3 than the center of the dimple 320.

The manner of forming the gas inlet holes 32 and the dimples 320 in the inner cover 3 will be described below with reference to FIGS. 8(a) to 8(c).

First, a press punch 44 is, as illustrated in FIG. 8(a), advanced from outside the inner cover 3 in a direction, as indicated by an arrow D, and pressed against a preselected portion of the straight side wall 301 until a desired domed shape is completed to form the dimple 320.

Next, a punch 45 is, as illustrated in FIG. 8(b), forced against a preselected portion of the dimple 320 in a direction, as indicated by an arrow E, to punch out the gas inlet hole 32, as illustrated in FIG. 8(c), in the dimple 320.

The formation of the dimples 320 results in an increased degree of freedom for orientation of the gas inlet holes 32 to direct a flow of the measurement gas to inside the inner cover 3 without a hit on the sensor element 2.

The gas inlet holes 32 are not equipped with a louver, like the one in FIGS. 11 and 12, and thus insensitive to damage arising from the concentration of thermal stress therearound. Specifically, the structure of the inner cover 3 is effective to avoid the direct hit of the gas flow on the sensing portion of the gas sensor element 2 and minimize the concentration of thermal stress on the inner cover 3 around the gas inlet holes 32.

The protective cover assembly 11 may alternatively include only the inner cover 3 which is disposed so that it is exposed directly to the measurement gas flowing outside the gas sensor 1.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor comprising:
   a hollow cylindrical housing having a first end and a second end opposite to the first end;
   a gas sensing element having a sensing portion, said gas sensing element being retained within said housing through a porcelain insulator to expose the sensing portion outside the first end of said housing;
   a cover secured at an end thereof to the first end of said housing to define a gas chamber to which the sensing portion of said gas sensing element is exposed, said cover having a dimple and a gas inlet hole, the dimple leading to a periphery of the gas inlet hole; and
   an outer cover which has a first and a second end opposite to the first end and is secured at the first end thereof to the first end of said housing and disposed outside said cover, said outer cover having a gas inlet hole through which a gas to be measured is admitted to the gas chamber.

2. A gas sensor as set forth in claim 1, wherein the gas inlet hole of said outer cover is located closer than the gas inlet hole of said cover to the second end of said outer cover.

3. A gas sensor as set forth in claim 1, wherein said cover has a tapered wall continuing to the end thereof joined to the first end of said housing, the tapered wall having a diameter which increases as the wall approaches the end of said cover, and wherein the gas inlet hole is formed in the tapered wall of said cover.

4. A gas sensor as set forth claim 1, wherein the dimple has a curved surface oriented to the gas inlet hole of said cover.

5. A gas sensor comprising:
   a hollow cylindrical housing having a first end and a second end opposite to the first end;
   a gas sensing element having a sensing portion, said gas sensing element being retained within said housing through a porcelain insulator to expose the sensing portion outside the first end of said housing; and
   a cover secured at an end thereof to the first end of said housing to define a gas chamber to which the sensing portion of said gas sensing element is exposed, said cover having a dimple and a gas inlet hole, the dimple leading to a periphery of the gas inlet hole, wherein the gas inlet hole of said cover has a peripheral edge oriented to a second end of said cover remote from the end joined to the first end of said housing, and wherein the dimple has a wall leading to the peripheral edge of the gas inlet hole of said cover.

6. A gas sensor comprising:
   a hollow cylindrical housing having a first end and a second end opposite to the first end;
   a gas sensing element having a sensing portion, said gas sensing element being retained within said housing through a porcelain insulator to expose the sensing portion outside the first end of said housing;
   a cover secured at an end thereof to the first end of said housing to define a gas chamber to which the sensing portion of said gas sensing element is exposed, said cover having a dimple and a gas inlet hole which is formed in the dimple; and
   an outer cover which is disposed outside said cover, said outer cover having a gas inlet hole through which a gas to be measured is admitted to the gas chamber.

7. A gas sensor as set forth in claim 6, wherein the gas inlet hole of said outer cover is located farther than the gas inlet hole of said cover from the first end of said housing.

8. A gas sensor as set forth in claim 6, wherein the dimple has a curved wall in which the gas inlet hole is formed.

9. A gas sensor comprising:
   a hollow cylindrical housing having a first end and a second end opposite to the first end;
   a gas sensing element having a sensing portion, said gas sensing element being retained within said housing through a porcelain insulator to expose the sensing portion outside the first end of said housing; and
   a cover secured at an end thereof to the first end of said housing to define a gas chamber to which the sensing portion of said gas sensing element is exposed, said cover having a dimple and a gas inlet hole which is formed in the dimple, wherein the dimple is of a domed shape.

* * * * *